US008384409B2

United States Patent
Kummel et al.

(10) Patent No.: US 8,384,409 B2
(45) Date of Patent: Feb. 26, 2013

(54) ULTRA-THIN ORGANIC TFT CHEMICAL SENSOR, MAKING THEREOF, AND SENSING METHOD

(75) Inventors: Andrew C. Kummel, San Diego, CA (US); Dengliang Yang, Union City, CA (US); William C. Trogler, Del Mar, CA (US); Thomas Gredig, Huntington Beach, CA (US)

(73) Assignee: The Regents of the University of California, Oakland, CA (US)

( * ) Notice: Subject to any disclaimer, the term of this patent is extended or adjusted under 35 U.S.C. 154(b) by 262 days.

(21) Appl. No.: 12/597,976

(22) PCT Filed: May 5, 2008

(86) PCT No.: PCT/US2008/005743
§ 371 (c)(1),
(2), (4) Date: Mar. 1, 2010

(87) PCT Pub. No.: WO2008/147497
PCT Pub. Date: Dec. 4, 2008

(65) Prior Publication Data
US 2010/0176837 A1   Jul. 15, 2010

Related U.S. Application Data

(60) Provisional application No. 60/927,470, filed on May 3, 2007.

(51) Int. Cl.
*G01R 31/02* (2006.01)
(52) U.S. Cl. .................. 324/762.01; 324/762.09; 257/40
(58) Field of Classification Search ............. 324/762.01, 324/762.09; 257/40
See application file for complete search history.

(56) References Cited

U.S. PATENT DOCUMENTS 5,448,905 A   9/1995   Stetter et al.
(Continued)

FOREIGN PATENT DOCUMENTS

KR   10-2004-0086196   10/2004

OTHER PUBLICATIONS

Wenping Hu, et al., "The gas sensitivity of a metal-insulator-semiconductor field-effect-transistor based on Langmuir-Blodgett films of a new asymmetrically substituted phthalocyanine," Thin Solid Films vol. 360, Dec. 2000, pp. 256-260.

(Continued)

*Primary Examiner* — Arleen M Vazquez
(74) *Attorney, Agent, or Firm* — Greer, Burns & Crain Ltd.

(57) ABSTRACT

An embodiment of the invention is an organic thin film transistor chemical sensor. The sensor includes a substrate. A gate electrode is isolated from drain and source electrodes by gate dielectric. An organic ultra-thin semiconductor thin film is arranged with respect to the gate, source and drain electrodes to act as a conduction channel in response to appropriate gate, source and drain potentials. The organic ultra-thin film is permeable to a chemical analyte of interest and consists of one or a few atomic or molecular monolayers of material. An example sensor array system includes a plurality of sensors of the invention. In a preferred embodiment, a sensor chip having a plurality of sensors is mounted in a socket, for example by wire bonding. The socket provides thermal and electrical interference isolation for the sensor chip from associated sensing circuitry that is mounted on a common substrate, such as a PCB (printed circuit board). A method of operating an organic thin film transistor chemical sensor exposes the sensor to a suspected analyte. A low duty cycle voltage pulse train is applied to the gate electrode to reduce baseline drift while sensing for a conduction channel change.

18 Claims, 3 Drawing Sheets

U.S. PATENT DOCUMENTS

| | | | |
|---|---|---|---|
| 5,719,033 | A | 2/1998 | Ackley et al. |
| 6,575,013 | B2* | 6/2003 | Bao et al. .................. 73/23.34 |
| 6,850,859 | B1 | 2/2005 | Schuh |
| 7,189,987 | B2 | 3/2007 | Bao et al. |
| 7,544,967 | B2* | 6/2009 | Kim et al. ..................... 257/40 |
| 2002/0117693 | A1 | 8/2002 | Dodabalapur et al. |
| 2002/0167003 | A1* | 11/2002 | Campbell et al. ............. 257/40 |
| 2004/0097813 | A1 | 5/2004 | Williams |
| 2004/0195563 | A1 | 10/2004 | Bao et al. |
| 2005/0189240 | A1* | 9/2005 | Lin et al. .................... 205/782 |
| 2007/0262303 | A1* | 11/2007 | Yan et al. ....................... 257/40 |

OTHER PUBLICATIONS

Ch. Pannemann, et al., "Nanometer scale organic thin film transistors with Pentacene," Microelectronic Engineering vol. 67-68, Dec. 2003, pp. 845-852.

Richard D. Yang, et al., "Ultrathin organic transistors for chemical sensing," Applied Physics Letters, vol. 90, Jun. 2007, pp. 263506(1).

Richard D. Yang, et el., "Ultralow drift in organic thin-film transistor chemical sensors by pulsed gating," Journal of Applied Physics, vol. 102, Aug. 2007, pp. 34515(1)-34515(4).

Bouvet, Marcel et. al., "Phthalocyanine-based field-effect transistor as ozone sensor", *Sensors and Actuators B*, 73, (2001) 63-70.

Bouvet, Marcel et. al., "Phthalocyanine-based field-effect transistor as gas sensor", *Anal Bionanal Chem*, (2006) 384: 366-373.

Chang, Josephine B., et. al., "Printable polythiophene gas sensor array for low-cost electronic noses", *Journal of Applied Physics*, 100, 014506 (2006).

Chang, Josephine B., et. al., "Effect of active layer thickness on bias stress effect in pentacene thin-film transistors", *Applied Physics Letters*, 88, 233513 (2006).

Crone, B., et. al. "Electronic sensing of vapors with organic transistors", *Applied Physics Letters*, vol. 78, No. 15, Apr. 9, 2001.

Dinelli, Franco, et. al., "Spatially Correlated Charge Transport in Organic Thin Film Transistors", *Physical Review Letters*, vol. 92, No. 11, Mar. 19, 2004.

Horowitz, Gilles, " Organic thin film transistors: From theory to real devices.", *Journal of Materials Research*, 19, pp. 1946-1962 2004.

Liao, Frank, et. al. "Organic TFTs as gas sensors for electronic nose applications", *Sensors and Actuators B*, 107 (2005) 849-855.

Miller, Karla a., et. al. "Electrode Independent Chemoresistive Response for Cobalt Phthalocyanine in the Space Charge Limited Conductivity Regime", *J. Phys. Chem B.*, 2006, 110, 361-366.

Ruiz, Ricardo, et. al. "Thickness Dependence of Mobility in Pentacene Thin-Film Transistors" *Adv Mater.*, 2005, 17, 1795-1798.

Schmechel, Roland, et. al., "Electronic traps in organic transport layers" *phys. stat. sol. (a)*, 201, No. 6, 1215-1235 (2004).

Someya, Takao, et. al. "Vapor sensing with a, w-dihexylquarterhiophene field-effect transistors: The role of grain boundaries", *Applied Physics Letters*, vol. 81, No. 16, Oct. 14, 2002.

Torsi, L., et al. "Multi-parameter gas sensors based on organic thin-film-transistors", *Sensors and Actuators B*, 67 (2000) 312-316.

Torsi, L., et al., "Organic Thin-Film Transistors as Plastic Analytical Sensors", *Anal. Chem*, Oct. 1, 2005, 77, (19) pp. 380A-387A.

Wang, Liang, et. al., "Nanoscale chemical sensor based on organic thin-film transistors", *Applied Physics Letters*, vol. 85, No. 26, Dec. 27, 2004.

Wright, John D., "Gas Adsorption on Phthalocyanines And Its Effects on Electrical Properties", *Progress in Surface Science*, vol. 31, pp. 1-60, 1989.

Yang, Richard et. al., "Chemical identification using an impedance sensor based on dispersive charge transport", *Applied Physics Letters*, 88, 074104, 2006.

Zhu, Zheng-Tao, et. al., "Humidity sensors based on pentacene thin-film transistors", *Applied Physics Letters*, vol. 81, No. 24, Dec. 9, 2002.

\* cited by examiner ic TFT CHEMICAL
ULTRA-THIN ORGANIC TFT CHEMICAL SENSOR, MAKING THEREOF, AND SENSING METHOD

PRIORITY CLAIM AND REFERENCE TO RELATED APPLICATION

This application claims priority under pursuant to 35 U.S.C. §119 from prior provisional application Ser. No. 60/927,470, filed May 3, 2007.

STATEMENT OF GOVERNMENT INTEREST

This invention was made with government support under AFOSR Contract No. F49620-02-1-0288 and NSF Contract No. CHE-0350571. The government has certain rights in the invention.

FIELD

A field of the invention is chemical sensing. A chemical sensor of the application has example applications including, for example, as a back-end detector for handheld gas chromatography; as a household or industrial sensor for detecting gas leakages; as an explosive vapor detector, and as a chemical warfare agent detector.

BACKGROUND

Chemical sensing is a critical process in a large number of everyday household, industrial, military, and scientific processes. A chemical sensor that can indicate the presence of a chemical of interest is useful to provide warnings, such as to indicate an unacceptable level of carbon monoxide or to provide a warning regarding the presence of an explosive vapor or a chemical warfare agent. Similarly, chemical sensors can provide information on the presence or absence of a particular chemical in a process control scheme. The presence or absence of a gas can provide feedback used to control a wide range of industrial processes. In the area of scientific research, many instruments including, for example, chromatography instruments benefit from sensitive chemical detectors.

Sensitivity is a critical aspect of chemical sensors. The more sensitive a sensor is, the lower level of chemical agent that it can detect. Accordingly, there is great interest in producing highly sensitive chemical sensors. Early warning regarding levels of sensed chemicals, faster control of processes responsive to particular levels of sensed chemicals, and better detection in difficult environments are achieved as sensitivity increases. Some particular example applications of interest in the art will now be discussed.

One application of interest is the detection of ultra-trace amounts of explosives and explosive-related analytes. Such detection is of critical importance in detecting explosives in a number of civilian and military or security applications, e.g., mine fields, military bases, remediation sites, and urban transportation areas. Low-cost and portability have clear additional advantages to such sensor applications.

In security applications, chemical sensors are preferable to other detection devices, such as metal detectors, because metal detectors frequently fail to detect explosives, such as those in the case of the plastic casing of modern land mines. Similarly, trained dogs can be both expensive and difficult to maintain in many desired applications. Other detection methods, such as gas chromatography coupled with a mass spectrometer, surface-enhanced Raman Spectroscopy, nuclear quadrupole resonance, energy-dispersive X-ray diffraction, neutron activation analysis and electron capture detection are highly selective, but are expensive and not easily adapted to a small, low-power package for broad distribution.

A particular type of chemical sensor that has been investigated is an organic thin film transistor (OTFT) that has its conduction channel affected in the presence of a chemical analyte. The general principal has been demonstrated, while typical efforts have not demonstrated a useful level of sensitivity. Example transistor chemical sensors are disclosed in the following articles. Torsi, et al., Sens. Actuators, B 67, 312 (2000). The channel material in Torsi et al was 1,4,5,8-naphthalene tetracarboxyl dianhydride. Channel thickness in the chemical sensor was 500 Å (>50 MLs); Crone, et al., Appl. Phys. Lett. 78, 2229 (2001) discloses a sensor with channel materials: of di-dodecyl a-6T. The thickness was 100-1000 Å (10-100 MLs). Someya, et al, Appl. Phys. Lett. 81, 3079 (2002) discloses channel materials: of DHa4T with thickness: 150 Å (15 MLs). Zhu, et al, Appl. Phys. Lett. 81, 4643 (2002), discloses channel materials of pentacene. The thickness was 500 Å (50 MLs).

Studies of the charge transport process in OTFTs have shown that carriers conduct primarily through the first 1-5 MLs above the gate dielectric. G. Horowitz, J. Mater. Res. 19, 1946 (2004). Prior OTFT sensors have not recognized or taken advantage of the charge carrier mechanism, having channel layers that are 10 monolayers or more, and typically 50 monolayers or more. Despite intensive study of OTFTs in chemical sensing, the transduction mechanism is not fully understood.

Another issue that impacts and limits usefulness of OTFT sensors is baseline drift. With static gate bias operation, even encapsulated OTFTs exhibit a large bias stress effect (BSE). This bias instability has been observed on OTFTs fabricated with a wide range of active materials and is associated with charge trapping in the organic film. Substantially delaying the time between measurements by hundreds of seconds reduces the BSE, but such a time delay is too long for many chemical sensing measurements. Baseline voltage compensation has also been considered, but simple baseline voltage compensation methods fail to reduce BSE.

SUMMARY OF THE INVENTION

Figure 1:
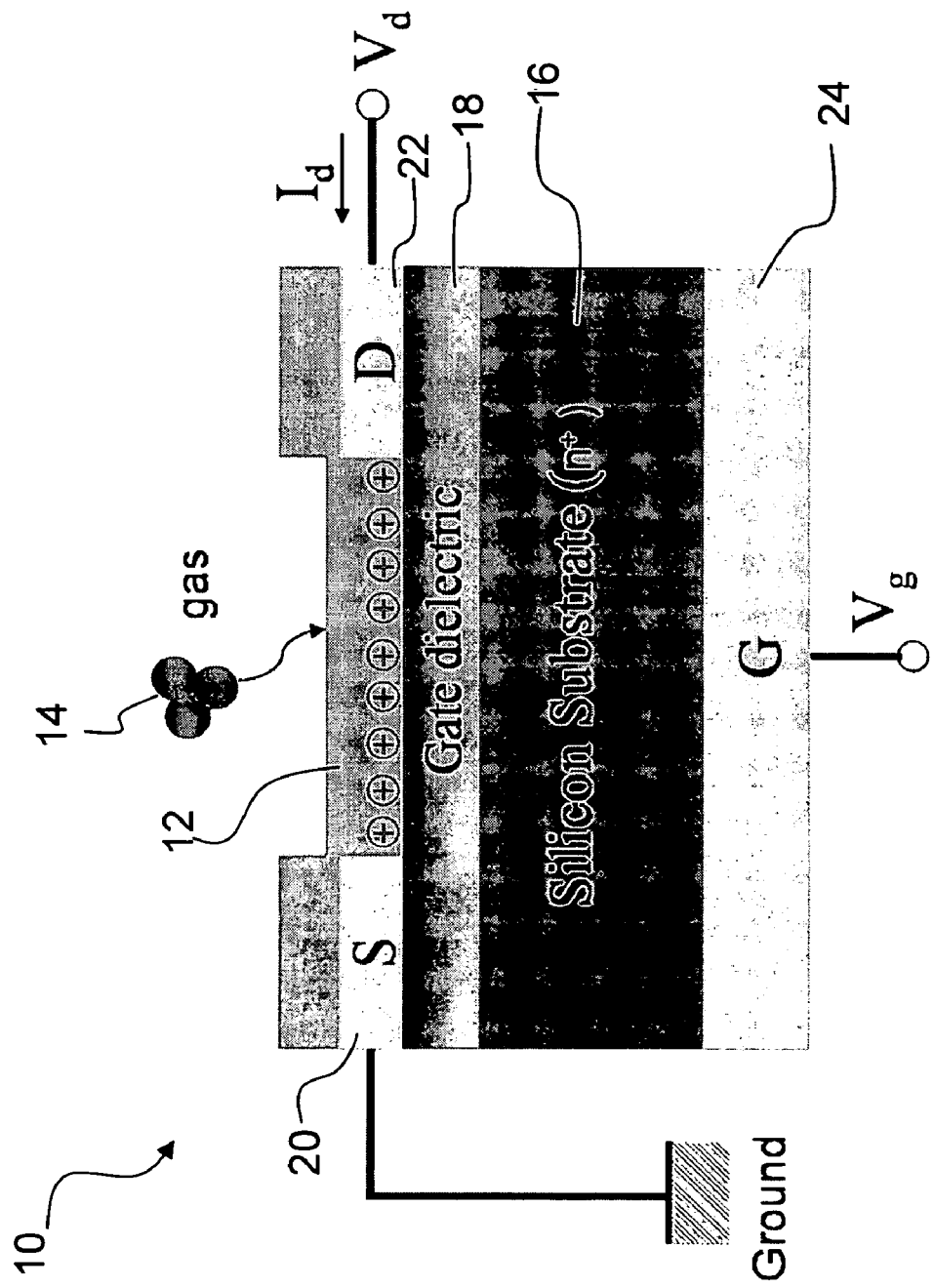
FIG. 1 illustrates a preferred embodiment organic ultra-thin transistor chemical sensor of the invention.

An embodiment of the invention is an organic thin film transistor chemical sensor. The sensor includes a substrate. A gate electrode is isolated from drain and source electrodes by gate dielectric. An organic ultra-thin semiconductor thin film is arranged with respect to the gate, source and drain electrodes to act as a conduction channel in response to appropriate gate, source and drain potentials. The organic ultra-thin film is permeable to a chemical analyte of interest and consists of one or a few atomic or molecular monolayers of material.

An embodiment of the invention is an organic ultra-thin film chemical sensor array system or package. An example sensor array system includes a plurality of sensors of the invention. In a preferred embodiment, a sensor chip having a plurality of sensors is mounted in a socket, for example by wire bonding. The socket provides thermal and electrical interference isolation for the sensor chip from associated sensing circuitry that is mounted on a common substrate, such as a PCB (printed circuit board).

A method of operating an organic thin film transistor chemical sensor exposes the sensor to a suspected analyte. A low duty cycle, less than 50% and preferably less than 10% voltage pulse train is applied to the gate electrode to reduce baseline drift while sensing for a conduction channel change.

A preferred method of fabricating an organic thin film transistor chemical sensor having a channel consisting of one or a few atomic or molecular monolayers includes forming a dielectric on a substrate. A gate contact is formed on the bottom of the substrate. Tapered source and drain contacts are formed while controlling the formation to avoid undercutting of the contacts. The source and drain contacts and gate dielectric are cleaned via ultrasonication. The one or a few monolayers of organic material are formed over the gate dielectric and source and drain contacts. The cleaning preferably is achieved with plural ultrasonications conducted in a sequence of trichloroethylene, acetone, and then isopropyl alcohol.

DETAILED DESCRIPTION OF THE PREFERRED EMBODIMENTS

An embodiment of the invention is an organic ultra-thin transistor chemical sensor having a channel that consists of one or a few monolayers. Organic thin film transistor chemical sensors of the invention have nearly monolayer thin film channels that act as super-sensitive detectors of trace levels of organic vapors. Sensors of the invention can act as simple, very sensitive chemical sensors, and can perform quantitative vapor analysis. An organic ultra-thin film transistor chemical sensor of the invention can, for example, detect toxic and flammable/explosive chemical vapors, and has obvious application to safety, security, and military applications.

An embodiment of the invention is an organic thin film transistor chemical sensor. The sensor includes a substrate. A gate electrode is isolated from drain and source electrodes by gate dielectric. An organic ultra-thin semiconductor thin film is arranged with respect to the gate, source and drain electrodes to act as a conduction channel in response to appropriate gate, source and drain potentials. The organic ultra-thin film is permeable to a chemical analyte of interest and consists of one or a few monolayers of material.

Method of fabrication of the invention provide sensors that can be reliably produced and perform reliably when conducting sensing. A preferred method of fabricating an organic thin film transistor chemical sensor having a channel consisting of one or a few atomic or molecular monolayers includes forming a dielectric on a substrate. A gate contact is formed on the bottom of the substrate. Tapered source and drain contacts are formed while controlling the formation to avoid undercutting of the contacts. The source and drain contacts and gate dielectric are cleaned via ultrasonication. The one or a few monolayers of organic material are formed over the gate dielectric and source and drain contacts. The cleaning preferably is achieved with plural ultrasonications conducted in a sequence of trichloroethylene, acetone, and then isopropyl alcohol.

An embodiment of the invention is an organic ultra-thin film chemical sensor array system or pack. An example sensor array system includes a plurality of sensors of the invention. In a preferred embodiment, a sensor chip having a plurality of sensors is mounted in a socket, for example by wire bonding. The socket provides thermal and electrical interference isolation for the sensor chip from associated sensing circuitry that is mounted on a common substrate, such as a PCB (printed circuit board).

A method of operating an organic thin film transistor chemical sensor exposes the sensor to a suspected analyte. A low duty cycle and low frequency voltage pulse train is applied to the gate electrode to reduce baseline drift while sensing for a conduction channel change.

An organic ultra-thin transistor chemical sensor system of the invention provides an output to indicate a level and/or quantity of chemical analyte sensed. A preferred system integrates a chemical sensor onto a platform that is suitable for mobile electronics applications. A portable sensor system includes electronics to interrogate the chemical sensor and monitor, for example, the conduction of its channel. The monitored property of the transistor is correlated to data indicating levels of chemical analyte that the chemical sensor is exposed to. Chemical sensors of the invention are stable, and can be used to conduct multiple tests while retaining sensitivity. The invention also includes methods of fabrication of an organic ultra-thin transistor chemical sensor. Integrated devices of the invention include, for example, a battery-operated handheld unit having one or more organic ultra-thin transistor chemical sensors packaged with electronics that drive testing and record and/or display information relating to the conduction in the transistor.

A preferred organic ultra-thin transistor chemical sensor is a field-effect transistor device with a semi conducting organic film as the active channel material, capable of absorbing chemical vapors. The channel conductance of the transistor changes at the presence of chemical vapors. The channel layer thickness has been reduced to a thickness of one or a few monolayers.

A preferred embodiment organic transistor chemical sensor having a monolayer channel provides what is believed to be the thinnest known channel materials for chemical sensing. Testing on prototypes reveals that the chemical response of a preferred sensor provides an enhancement up to a factor of 15 compared to thick devices made of the same material and geometry. Additionally, a baseline drift smaller than 0.025%/hr at the presence of chemical analytes has been demonstrated in prototype devices.

Preferred embodiments of the invention will now be discussed with respect to the drawings. The drawings may include schematic to representations, which will be understood by artisans in view of the general knowledge in the art and the description that follows. Features may be exaggerated in the drawings for emphasis, and features may not be to scale.

FIG. 1 shows an example embodiment organic thin-film transistor chemical sensor 10. The sensor 10 includes an organic thin film channel 12 that is one or a few atomic or molecular monolayers and is extremely sensitive to analyte, such as a gas analyte 14. The example embodiment chemical sensor 10 is formed on a silicon substrate 16. While the example embodiment is a silicon based device, other material systems can also be used. Gate dielectric 18, e.g., silicon dioxide, isolates source 20 and drain 22 electrodes, and a gate electrode 24 is formed on an opposite side of the substrate 16.

The thin film channel 12 in the organic thin-film transistor chemical sensor 10 is formed by an organic semiconductor ultra-thin-film, which serves as the charge transport layer of the organic thin-film transistor chemical sensor 10. A variety of organic materials are suitable. Preferred materials include copper phthalocyanine (CuPc), $CuC_{32}N_8H_{16}$, cobalt phthalocyanine (CoPc), $CoC_{32}N_8H_{16}$, metal-free phthalocyanine ($H_2Pc$), $C_{32}N_8H_{18}$, Copper-Hexadecafluorophthalocyanine ($F_{16}CuPc$)($F_{16}CuC_{32}N_8H_{16}$).

At appropriate gate (Vg) and drain (Vd) voltages, a conduction channel forms above the gate dielectric 18. The adsorption of analyte, e.g., the analyte gas 14, on the surface of the ultra-thin-film modulates the channel conductance. This produces a chemical signal response that can be electrically read, either by DC or AC measurements. The channel thickness is one or a few monolayers (<=4 MLs). Due to the active participation of analyte in the charge transport of carriers provided by the ultra thin channel 12, chemical response enhancement up to a factor of 15 has been observed in prototype devices. Prototype devices in accordance with FIG. 1 have shown reduced baseline drift at the presence of analytes to less than 0.025%/hr.

Various organic semiconductors that can be formed as thin films are suitable to for the ultra thin channel 12. Examples include cobalt phthalocyanine (CoPc), Copper Phthalocyanine (CuPc), Copper-Hexadecafluorophthalocyanine ($F_{16}CuPc$) and Metal-free phthalocyanine ($H_2Pc$), where $Pc=C_{32}N_8H_{16}$. A number of organic semiconductor films have been tested, and the experimental results are discussed below.

Figure 2:
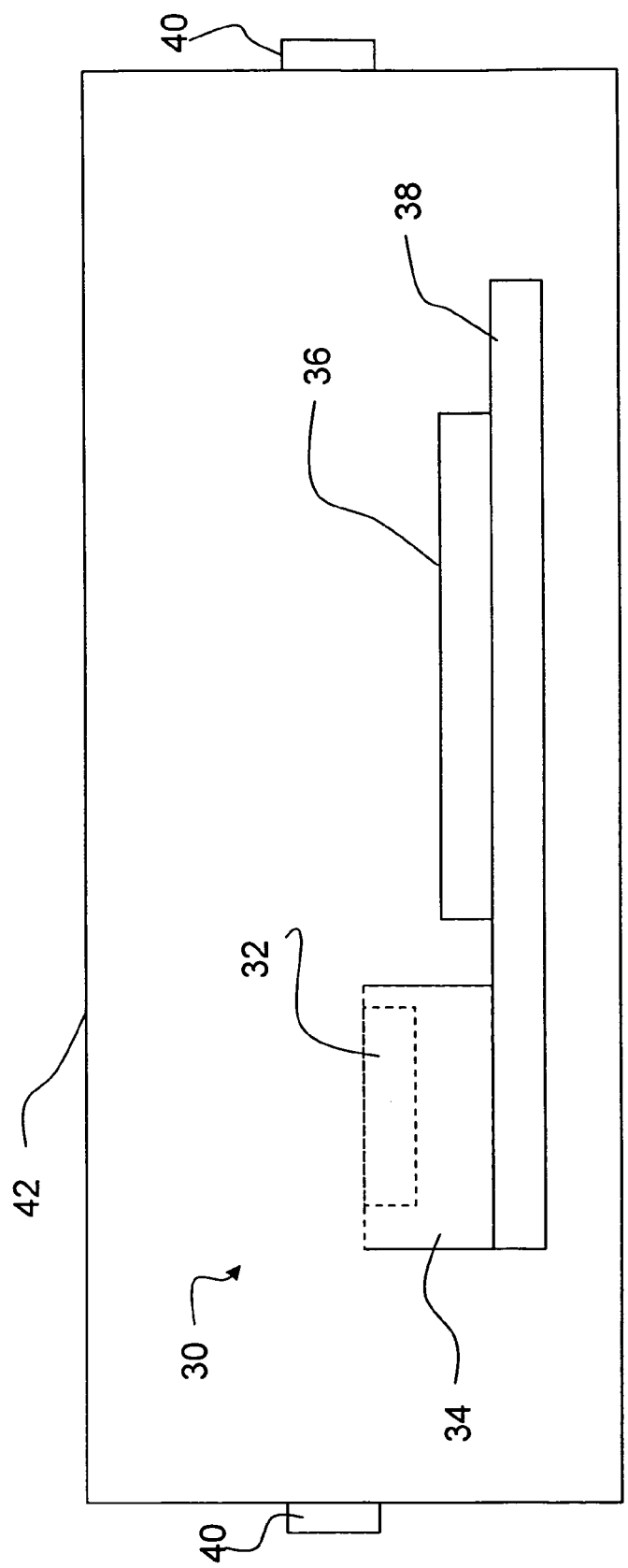
FIG. 2 illustrates a preferred embodiment organic ultra-thin transistor chemical sensor array system of the invention.

An embodiment of the invention is an organic ultra-thin film chemical sensor array system or package. An example sensor array system 30 is shown in FIG. 2, and includes a plurality of sensors of the invention. An example includes a sensor chip 32 having a plurality of sensors 10 (see FIG. 1) that are mounted in a socket 34, such as by wire bonding. The socket provides thermal and electrical interference isolation for the chip 32 from associated circuitry 36 that is mounted on a common substrate 38, such as a PCB (printed circuit board). The PCB mounting arrangement permits, for example, the sensing system including the sensor array 30 and circuitry 36 to be incorporated into a handheld device. The circuitry 36 preferably includes circuits for driving testing for chemical analytes, receiving results from the chemical sensors, storing testing information, generating displays, etc.

Interconnections between the circuitry 36 and the chip are through conventional PCB connections, and the PCB can also include circuitry related to a device that the sensor array 30 is being incorporated into. Prototype 6-pack sensor arrays demonstrated the FIG. 2 packaging arrangement to be repeatable for over 10 organic transistors made of three different materials and deposited at five different conditions. Prototype arrays demonstrated efficacy in detecting both high and low volatility organic vapors.

Figure 3A:
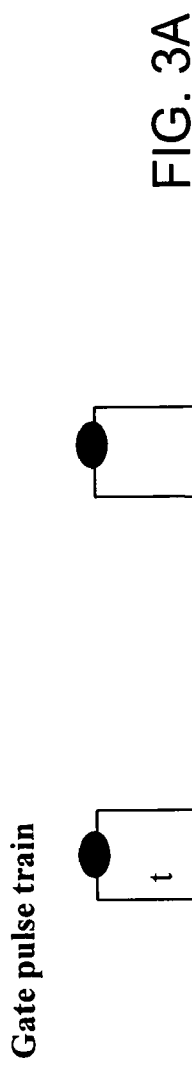
FIGS. 3A-3C illustrate a preferred embodiment method of controlling baseline drift via pulsed gate control.
Figure 3B:
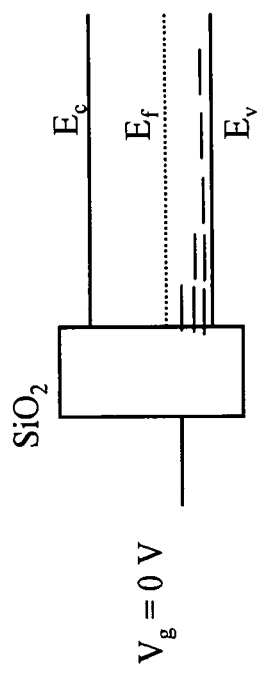
Figure 3C:
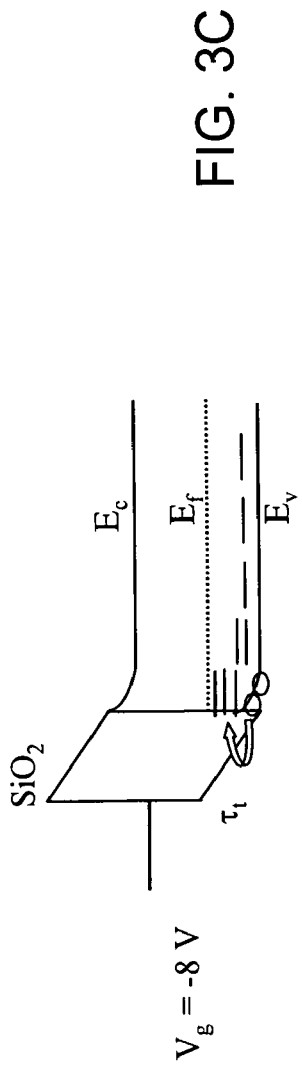

A particular method of operation of the organic ultra-thin transistor chemical sensor 10 or the organic ultra-thin transistor chemical sensor array system 30 maintains very low baseline drift by applying a low duty cycle, less than 50% and preferably about 10% or less, gate pulse train on the gate electrode. A low frequency signal is also preferred, less than 100 Hz and preferably below about 10 Hz, to keep the transistor operation close to its DC characteristics. FIGS. 3A-3C illustrate a method of controlling baseline drift. The band diagrams of the "off" and "on" states are shown at different voltages in FIGS. 3B and 3C. Break lines represent trap states located near the $SiO_2$ interface and in the bulk. FIG. 3A illustrates a pulse train applied to the gate electrode that varies between 0V and −8V. FIGS. 3B and 3C illustrate the corresponding energy levels. In FIG. 3B the gate dielectric is silicon dioxide. Ev, Ec and Ef represent the energy levels for the valance band, conduction band and the Fermi level energy, respectively. The dashed lines above Ev represent energy levels that are occupied by charge traps. With applied gate potential, Ev is closer to Ef, and the organic-$SiO_2$ interface is populated with more charge carriers. These charge carriers will occupy energy levels of trap states at a trapping rate of $\tau_r$. By reducing the time that the gate voltage ($V_g$) is applied, the unwanted charge population trapped in these trap energy levels can be reduced. Therefore, the pulsed operation reduces the bias stress effect (BSE). As seen in FIGS. 3B and 3C, the charge carriers are transported in a few monolayers adjacent to the gate oxide; therefore, the relevant trap energy $E_a$ comes from the organic thin film/gate dielectric interface. Consequently, in thick films, the effect of the analyte on the relevant $E_a$ is minimal, because the analytes affect only the trap energies far from this interface. Conversely, in the organic ultra-thin transistor chemical sensor of the invention, the air/organic thin film surface is near the gate dielectic/organic thin film interface so that the surface trap states affect the charge transport even at very high gate voltage.

At 0 V gate bias (FIG. 3B), the device is assumed to rest in flat band condition. There is no charge accumulation in the channel at this bias condition. The flat band voltage depends on the threshold voltage of the devices, which is 0 V for the device represented in FIGS. 3A-3B. Conversely, at −8 V (FIG. 3C), hole carriers are accumulated in the channel by the gate capacitor. Carriers are trapped in states within the band gap at different rates depending on the capture cross-section of trap states. For gate bias pulses between 0 V and −8 V, the device goes between flat band and accumulation conditions. There is a finite charge trapping time $\tau_t$ for the trap states to capture holes. If the gate stress time t is less than $\tau_t$, the charge trapping effect can be greatly reduced.

In preferred embodiments, a low duty cycle analyte dose, preferably about 10% or less, is combined with a low duty cycle pulsed gating. This permits the baseline drift for low vapor pressure analytes to be reduced to a level similar to those attained for highly volatile analytes. In a preferred embodiment, the circuitry 36 (FIG. 2) also controls valves 40 to an enclosure 42 that is part of an analyte testing to control analyte pulses in addition to gate pulses.

No auto zeroing is required to reset the chemical sensor with the low duty cycle gate pulse train operation. Embodiments of the invention can maintain a constant baseline of operating chemical sensor in one day to a week or substantially longer. Accordingly, there is no requirement to change operating bias to reset the device. Therefore, the chemical response does not change over time. Typically, chemical sensors require auto-zero from time to time and need re-calibration over time. Without the need for auto-zero and re-calibration, there is no need, as is sometimes done in the art, to use a reference device made of the same materials. Thus, calibration error induced by process variation in device fabrication is nulled. A pulsed gating train is applied on the gate electrode instead of using a static gate.

Experiments

Experiments have been conducted to test embodiments of the invention. Additional features and embodiments of the invention will be apparent from the discussion of experiments that were conducted, while artisans will also appreciate broader aspects of the invention from the experiments.

Ultrathin Channel Cobalt Phthalocyanine Transistor Sensor Experiments

Working prototypes have been fabricated. Ultra-thin (4 monolayers, or 5.2 nanometers) and thicker (considered thin film in the art) (50 monolayers, or 65 nanometers) organic transistors in accordance with the FIG. 1 structure have been fabricated with cobalt phthalocyanine (CoPc) as the channel material. Example films include organic thin-films such as CuPc, CoPc and $H_2Pc$. Prototype CoPc devices in accordance with the invention having the 4 mL channel reduced baseline drift by 12 times compared to devices having 50 mL channels. The organic ultra-thin transistor chemical sensors of the invention also show faster response times, higher baseline stabilities in the presence of analytes, and sensitivity enhancements of 2-16 for five analytes tested, which included EA (ethyl acetate), TE (toluene), DIMP (diisopropylmethylphosphonate), NB (nitrobenzene) and MeOH (methanol). The absorption of analytes changes both the surface doping level and trap energies. It is believed that the changes in surface trap energy greatly perturb the charge transport properties of the ultrathin devices, thereby, making these devices more sensitive. The CoPc films as thin as 4 MLs were deposited both by organic molecular beam epitaxy (OMBE) and in a thermal evaporator.

It is believed that the changes in surface trap energy affect the charge transport more strongly in thin devices because the charge transport layers are closer to the air/CoPc interface as compared to the thick devices. The observed improvements in baseline stability and dynamic response to gas sensing confirm the active participation of the surface traps in charge transport in the ultrathin transistors.

The CoPc used in the experiments was purchased from Sigma-Aldrich and purified by zone sublimation below $10^{-5}$ Torr. Bottom-contact devices were fabricated on highly doped n++($>10^{18}$ $cm^{-3}$P) silicon wafers with 100 nm of thermally grown $SiO_2$. The channel length and width of the devices were 10 µm and 2 mm respectively. CoPc thin films of 4 mL and 50 mL were deposited by OMBE at pressure of $2\times10^{-9}$ Torr at 80° C. Similar results were obtained from 4 mL thin CoPc films deposited by thermal evaporation at a pressure of $2\times10^{-7}$ Torr at 80° C. Chemical sensing experiments were performed inside a custom built computer controlled flow system. Chemically selective materials, such as CoPc generally have several orders of magnitude lower mobility than materials typically employed in the ultrathin OTFTs. Very careful control of the taper of the gold electrodes to avoid undercutting of the electrodes and three cycles of ultrasoniccation in trichloroethylene/acetone/isopropyl alcohol cleaning are preferably used to ensure excellent contact between the thin film organic channel along electrodes. Taper in the electrodes (a >90 degree angle relative to the gate dielectric) can be achieved by a number of methods. On preferred method is one example is to use a bilayer photoresist process with two different photoresists and develop the photoresistors in two different solvents to achieve <90 degree slope pattern that translates to a >90 degree electrode slope. A preferred bilayer process is disclosed in Kummel et al., "Bilayer Processing for an Enhanced Organic-electrode Contact in Ultrathin Bottom Contact Organic Transistors", APPLIED PHYSICS LETTERS 92, (2008).

The devices were characterized in an optically isolated chamber at 25° C., to minimize the photocurrent effect. Each device was stabilized in a dry air flow for three days prior to chemical response measurements to stabilize doping from atmosphere oxygen and humidity. For each film thickness, six devices were deposited simultaneously, and the mobility variation was less than 5% with the same operating voltages. Mobility values extrapolated from the linear region of operation were determined to be $1.0\times10^{-4}$ $cm^2/Vs$ and $2.6\times10^{-4}$ $cm^2/Vs$ for the 4 ML and 50 ML device, respectively. The lower mobility of the 4 mL device may be due to incomplete film coverage above the third layer or differences in film texture. The threshold voltages are +0.38 V and −0.38 V for the thin and thick device, respectively.

Typical nominal film thickness was determined by X-ray diffraction (XRD) to be 3.8 MLs (51 Å). The d-spacing is 13.3 Å in accordance with previous measurements that show the molecular planes of CoPc are oriented perpendicular to the substrate surface. The surface morphology measured by atomic force microscopy (AFM) shows that CoPc thin-film grown at 80° C. has an average grain size of 36 nm and the surface RMS roughness from AFM is 6.6 Å (for the bare substrate it is 0.9 Å). By combining the average height from the AFM (2.3 nm) with the average thickness from the XRD data, it can be inferred that there are two complete MLs of CoPc in these example experimental devices. The target during deposition in the experiments was a 4 ML nominal thickness, which resulted in 2 continuous ML coverage on the gate dielectrics. The average film thickness of the discussed film is 4 ML, but at some places, it is only 2 ML, while at other places it is 6 ML thick.

For determination of the chemical response and dynamic response, experimental devices were exposed to 25 chemical pulses, each exposure was 20 minutes long and followed by a 40 minute recovery in a dry air flow. To minimize bias stress, a 0.5 Hz pulsed, 1% duty cycle gate bias was used for both devices. Three analytes were chosen to represent stimulants for nerve gases (DIMP), explosives (nitrobenzene) and volatile organic vapors (methanol). Two other volatile organics, ethyl acetate and toluene, were also tested in the same manner for comparison of chemical responses between thin and thick devices. The chemical response is defined as $$R \equiv \frac{I_{analyte} - I_0}{I_0} * 100\%,$$

where $I_0$ is referred to the initial drain current.

The 4 ML device shows enhanced chemical response to all the analytes compared to the 50 ML device. The average enhancement factors ($R_{4ML}/R_{50ML}$) for NB, MeOH, ethyl acetate, DIMP and toluene are 15.8, 4.0, 2.2, 1.9 and 1.7, respectively. Any linear correlation between the enhanced chemical response and a molecular property, such as dipole moment or vapor pressure, was not readily apparent. The tests infer that the analyte interaction with the surface sites is a complex function of analyte dipole, polarizability, ligand length and molecular structure.

The chemical sensitivity of the two devices has been calculated by dividing chemical response over analyte concentration. As shown in Table I, CoPc organic ultra-thin transistor chemical sensors are one order of magnitude more sensitive to NB and DIMP as compared to other organic volatile vapors. The results imply that CoPc organic ultra-thin transistor chemical sensor are good sensors for detecting nitroaromatic and organophosphonate analytes.

Diluted NB concentrations as low as 75 ppb (parts per billion) were detected using the ultrathin device. The test is limited by the accuracy of our smallest mass flow controller (2% of 10 sccm). The 75 ppb dose of nitrobenzene gave a relative response of 0.1% of the 2.70 µA output current in the 4 ML transistor. This chemical sensitivity is among the best reported for nonredox active reducing analytes on chemFETs.

All five analytes reduced the drain current in both thin and thick films. The output current decrease is a result of the lower concentration of free carriers. This loss of free carriers can be ascribed to a reduced "surface doping" concentration, an increased trap energy, or both.

The relationship between trap energy and analyte response can be quantified. At high gate voltage ($-8$ V), $V_g \gg V_t$, where electronic theory of gas adsorption on semiconductor surfaces, which correlates gas desorption/adsorption rates with the film's Fermi levels.

Table I below shows the chemical sensitivity (S) in %/ppm (ppm=parts per million), drift (D) in %/h and response time $t_{50}$ in second of 4 ML and 50 ML devices. The analytes are presented in order of sensitivity. The uncertainty of S, D and $t_{50}$ calculation are $\pm 10$%.

TABLE I

| | NB | | | DIMP | | | MeOH | | | Toluene | | | EA | | |
|---|---|---|---|---|---|---|---|---|---|---|---|---|---|---|---|
| Device | S | D | $t_{50}$ | S | D | $t_{50}$ | S | D | $t_{50}$ | S | D | $t_{50}$ | S | D | $t_{50}$ |
| 4 ML | 1.343 | 0.05 | 108 | 0.03 | 0.05 | 164 | 0.007 | 0.00 | 20 | 0.0030 | 0.03 | 500 | 0.0015 | 0.05 | 540 |
| 50 ML | 0.086 | 0.18 | 466 | 0.02 | 1.15 | 360 | 0.002 | 0.58 | 79 | 0.0018 | 0.03 | 529 | 0.0009 | 0.03 | 606 |

$V_t$ ($-0.5$ V to $0.5$ V) is the threshold voltage, the current is linearly proportional to the mobility and gate voltage. Therefore, the chemical response is mainly determined by the change in mobility at a fixed $V_g$, $$R = \frac{\Delta I}{I_{base}} = \frac{\Delta \mu}{\mu_{base}},$$

where $\Delta\mu = \mu_{analyte} - \mu_{base}$. The effective mobility is related to trap energy $E_a$ as $$\mu = \mu_0 \exp\left(\frac{-E_a}{kT}\right) \quad (1)$$

where $\mu_0$ is the mobility related to the dopant concentration. OTFT conductivities are modeled as a trap mediated conductivity so the carrier density does not appear explicitly in the equation and instead is incorporated into the mobility term. In OTFTs, the charge carriers are transported in a few MLs adjacent to the gate oxide; therefore, the relevant trap energy $E_a$ comes from the CoPc/SiO$_2$ interface. Consequently, in thick films, the effect of the analyte on the relevant $E_a$ is minimal, because the analytes affect only the trap energies far from the CoPc/SiO$_2$ interface. Conversely, in ultrathin films, the air/CoPc surface is near the CoPc/SiO$_2$ interface so that the surface trap states affect the charge transport even at very high gate voltage. The greatest enhancement for the response was observed for nitrobenzene, which should be a good hole trap since it has the largest dipole moment of the five analytes and probably the largest polarizability.

The reduced baseline drift in the presence of analytes in ultrathin films may be attributed to the close location of the surface trap states to the gate dielectric. In ultrathin devices, the potential gradient from the gate is sufficiently strong and close to the oxide/CoPc interface that it tends to remove positive charges from the surface trap states, thereby, reduces irreversible trapping that produces baseline drift.

Faster dynamic response in ultrathin sensors is also shown in Table I. The turn-on response $t_{50}$ is quantified by the time takes to reach 50% of the maximum chemical response. While the response times for ethyl acetate and toluene decrease by only 10%, for three simulants analytes, the response time $t_{50}$ is three times less in the 4 ML devices compared to the 50 ML devices. The $t_{50}$ for the most volatile analyte, methanol, is 20s which is limited by the chamber response time. This result is consistent within the frame of the Pulsed Gating Experiments for Ultrathin Channel Sensor Transistors Trap states in organic films are a major source of the electrical instability in organic thin film trantistors causing baseline drift under static gate bias. The phenomenon has been identified as the bias stress effect (BSE), and at a macroscopic level, it is related to charge trapping induced shifts in threshold voltage. BSE under static gate bias conditions typically reduces baseline current by 60% over 20 h on the phthalocyanine based OTFT sensors. The baseline drift has been reduced to 1% over 20 h in the absence of analyte using the pulsed gating method of the invention. Pulsed gating is compatible with chemical sensing, since mass transport limits the time resolution of chemical sensors. With pulsed gating, the baseline drift on exposure to 15 methanol pulses is less than 0.09%/h and the response to this analyte is fully recoverable. Similar ultra-low drift results were obtained for methanol sensing on three different phthalocyanine OTFTs. Combining the pulsed gating with low duty cycle analyte pulses, this method is also applicable to obtain ultra-low drift for low vapor pressure analytes, such as organophosphonate nerve agent simulants.

The organic channel materials used in experiments were metal phthalocyanines with copper or cobalt metal centers (CuPc or CoPc) and the metal-free phthalocyanine (H$_2$Pc). The thicknesses of the organic thin films were between 4-50 monolayers (MLs). CuPc, CoPc and H$_2$Pc materials were purchased from Aldrich and purified three times by zone sublimation. Bottom-contact devices were fabricated on n$^+$ silicon wafers with 100 nm of thermally grown SiO$_2$. Gold was evaporated onto the back of the silicon wafers to form to the gate electrode. The channel length and width of the devices were 10 mm and 2 mm, respectively, defined by a photolithography process. Interdigitated electrodes with 25 pairs of fingers were used to increase the output current.

CuPc, CoPc and H$_2$Pc films were deposited by organic molecular beam epitaxy at 80° C. at rate between 0.4 Å/s to 1 Å/s. The films were 20 ML CuPc, 4 ML CoPc, 50 ML CoPc, and 25 ML H$_2$Pc. The film thicknesses were measured by quartz crystal microbalance during deposition, and calibrated by atomic force microscopy and x-ray diffraction measurements. The d-spacing is 13.3 Å. Six duplicate devices were deposited for each device under investigation. No annealing was performed on the deposited devices, but all devices were exposed to air for at least one month prior to use to ensure repeatable chemical response in air. The six devices had only 5% variation in electrical conductivity and chemical sensing response. All the devices were p-channel transistors and had threshold voltages between $-0.38$ V to $+0.38$ V. Mobility values extracted in linear operation regions were between $2.0\times10^{-5}$ cm$^2$/Vs and $2.6\times10^{-4}$ cm$^2$/Vs.

The electrical properties of the devices were measured using a Keithley 6385 picoammeter and programmable Agilent E3631A power supply. The electrical measurement system was calibrated with a HP 4156B precision semiconductor parameter analyzer. For the pulsed measurement at different frequencies, a specially built transient spectroscopy system has been developed utilizing National Instrument's 6040E DAQPad and a FEMTO DLPCA-200 variable gain low-noise current amplifier. The transient spectroscopy system was also calibrated with the HP 4156B parameters analyzer.

Chemical sensing experiments were carried out inside a custom-built flow system controlled by a computer. The devices were loaded inside the optically-isolated chamber under dry air flow for 2 days before testing to eliminate photocurrents and doping by $H_2O$, $O_3$, and other ambient reactive trace gases. The temperature in the chamber was kept at 27±0.2° C. using a Haake constant temperature bath. Bubblers filled with liquid analyte were kept in a water bath chilled to 15° C. Mass flow controllers were used to dilute and introduce analyte vapors at a known concentration into a manifold, where they were premixed and diluted with the carrier gas before introduction into the test chamber. Solenoid valves before and after the analyte bubblers were used to prevent cross-contamination between analytes. A four-way valve was used to minimize the dead time between the introduction of each analyte pulse. The analytes employed were methanol, diisopropyl methylphosphonate (DIMP) and dimethyl methylphosphonate (DMMP) at a constant flow rate 500 sccm in dry air. All the devices have been found to have stable output characteristics for one year after fabrication. However, the electrical noise of all the device devices increase after of one month intense testing. The increase in noise was more severe for the ultrathin devices and was consistently observed for all the ultra-thin devices. Replacing the cables or resoldering the leads to the contact pads does not reduce the increased noise. The electrical noise is likely due to the aging of contacts between organic films and metal electrodes.

Experiments were conducted to eliminate baseline drift in the CuPc devices without chemical analytes. Using relatively short test periods (2 h), the effect of the gate duty cycle on the baseline stability was measured as a function of gate duty cycle and frequency to find an optimized operating condition. Subsequently, the optimal pulse cycle was applied in a testing period of 20 h to measure the long term baseline stability. The pulsed gating was also tested in the absence of analyte on devices made of two other phthalocyanine materials.

Other experiments tested the impact of BSE on CuPc device baseline stability was quantified by comparing responses to methanol vapor pulses under static vs. pulsed gating.

In additional experiments, the pulsing method was applied for device detection of low vapor pressure organophosphonate nerve agent simulants. The analyte pulse duty cycle has been varied to separate analyte-induced baseline drift from electrical induced drift and to reduce the analyte induced drift to negligible levels.

A. Optimal Gate Pulse Selection

Drain current was measured over 2 h in the absence of analytes. The CuPc device devices were loaded in the chamber for two days and fully relaxed from bias stress. Gate pulse trains of 0.1 Hz were applied at the gate electrode between duty cycles of 1%-100%. The "on" gate voltage was fixed at −8V while the "off" gate voltage was fixed at 0 V.

Tests showed that under static gate bias (100% gate duty cycle), the baseline drifted 25% after 2 h. The baseline drift with 1% gate duty cycle was less than 0.1% over 2 h, which is 250 times less than for the static gate bias. During the tests, the drain voltage was held at constant (−4 V). Baseline drift was not observed at the low gate duty cycle. Therefore, bias stress due to static drain bias can be excluded as a cause of BSE in these devices.

The percentage baseline drift as a function of the pulse duration was calculated. For 0.1 Hz gate pulses, the baseline drift over 2 h rose above 1% only for pulse durations greater than 1 sec. Baseline drift was also measured at constant pulse duration (100 ms) while varying the frequency of the pulses between 0.05 Hz to 5 Hz. Baseline drift in 2 h rose above 1% for pulse frequencies above 1 Hz. Further reducing the pulse duration to keep the duty cycle constant increases the noise. For subsequent measurements, the pulse frequency was held at 0.1 Hz.

To test the feasibility of the pulsed gating method for continuous operation of devices, the baseline stability of the devices was compared over a period of 20 h. The drain current has been measured a with −8V gate voltage pulsed at 0.1 Hz (1% duty cycle) and contrasted with results for a −8 V static gate, and a −4 V static gate. The baseline drift was found to be less than 1% over 20 h with pulsed gating. Conversely, the baseline drift was 55% over 20 h for a static gate bias at −8 V. Reducing the static gate bias by half to −4V only reduced the drift with the static gate from 55% to 38% over 20 h. The results indicate that the baseline drift problem can be effectively solved by the pulsed gating method.

Pulsed gate operation was tested on CoPc and $H_2$Pc devices to demonstrate its usefulness in organic thin film transistor sensors formed from other channel materials. The same gate pulse train (0.1 Hz, 1% duty cycle, −8V) employed for the 20 mL CuPc device was applied in the measurements. For channels of all three materials and for all channel thicknesses tested (4 ML to 50 ML), the pulsed gating operation reduced the baseline drift to 0.05%/hr. In all the above measurements, the rest gate voltage was set at 0 V, which is within 0.5 V of the threshold voltages for all the above devices. The threshold voltages of the 50 ML and 4 ML CoPc devices are −0.38 V and +0.38 V, respectively. The 0 V rest voltage causes a positive drift in the 50 ML CoPc device, while a negative drift occurs in the 4 ML CoPc device. For devices with non-zero threshold voltage, the rest gate voltage needs to be set close to the threshold voltage to minimize the bias stress at rest gate bias. The rest gate voltage is the gate voltage when the sensor conduction channel is not turned on.

At 0 V gate bias, the device is assumed to rest in flat band condition. There is no charge accumulation in the channel at this bias condition. The flat band voltage depends on the threshold voltage of the devices, which is 0 V for the device represented in FIGS. 3A-3B. Conversely, at −8 V, hole carriers are accumulated in the channel by the gate capacitor. Carriers are trapped in states within the band gap at different rates depending on the capture cross-section of trap states. For gate bias pulses between 0 V and −8 V, the device goes between flat band and accumulation conditions. There is a finite charge trapping time $t_t$ for the trap states to capture holes. If the gate stress time t is less than $t_t$, the charge trapping effect can be greatly reduced. The phenomenon was observed on all devices that were tested. The obtained results were consistent with a charge trapping time between 1 and 2 s in the 20 ML CuPc devices.

To confirm that the bias stress is a charge trapping process in the organic channel instead of in the gate oxide, the change in output current versus time was analyzed. The kinetics of BSE is usually modeled from the time dependent threshold voltage shift. The evolution of threshold voltage in the 20 ML CuPc device can be calculated from obtained data concerning time dependent drain current. In the linear region, the drain current of OTFT is $$I_d = \frac{W}{L} C_i \mu (V_g - V_t) V_d \quad (4)$$

where $C_i$ is the gate capacitor, W and L is the transistor width and length and µ is the effective field-effect mobility. The mobility has been found to be constant during the bias stress experiments. Based on the above assumption, the threshold voltage shift can be deduced from the drain current as following, $$V_t(t) = V_{to} - (I_d(t) - I_{do}) / \left(\frac{W}{L} C_i \mu V_d\right) \quad (5)$$

where $V_{to}$ and $I_{do}$ are the initial threshold voltage and drain current. The kinetics of BSE at $V_g = -8$ V has been fitted with a power law dependent function, $$\Delta V_t = -0.333(t)^{0.32}, \text{ with } R^2 = 0.9999. \quad (6)$$

Similarly, the BSE at $V_g = -4$ V can be well fitted by the power law with a power coefficient 0.27. On amorphous silicon TFTs, it has been experimentally found that charge trapping in the gate dielectrics follows logarithmetic kinetics while charge trapping in the a-Si channel follows the power law kinetics. The bias stress presented above has a power law dependence and a time scale consistent with the charge trapping effect in the organic channel.

B. Baseline Drift with High Volatility Analyte

The baseline stability of the 20 ML CuPc devices in the presence of high volatility analytes was tested. Highly volatile analytes were employed to insure that the chemically induced drift due to accumulation of analyte by the organic film is negligible and that all drift is due to electrical instability. A comparison was made between static and pulsed gating operation of the devices exposed to 15 methanol chemical pulses. Each chemical pulse is 20 minutes long followed by 1 h recovery. With 1% duty cycle, 0.1 Hz gate pulsing at −8V, the chemical response was found to be fully reversible. A mean baseline drift value was calculated by measuring the accumulated drift for each of the 15 pulses referenced to the same starting point. The baseline drift was 0.09±0.016%/h within the 20 h test duration, which is comparable within a factor of two to the rate of drift observed in the absence of analyte. Similar ultra-low baseline drift to methanol pulses has been found with the CoPc and $H_2Pc$ devices. Conversely, with a static gate bias, the baseline drifted over 60% during 20 h of methanol pulsing.

The electrical instability under static gate bias also impairs the accuracy of chemical sensitivity measurement. For the 1% duty cycle, 0.1 Hz pulsed gating, the chemical sensitivity to methanol is $4.05+/-0.03 \times 10^{-3}$%/ppm. For static gate operation, the chemical sensitivity is $4.33+/-0.34 \times 10^{-3}$%/ppm without correcting for baseline drift. Bias stress increased the uncertainty in chemical sensitivity measurements by a factor of 10. The increased chemical sensitivity uncertainty with static gate bias is due to the nonlinear behavior of the bias stress effect. Even though the baseline of devices in the absence of analytes is highly repeatable, and can be well fitted with the power law, the exposure to analyte changes the kinetics, which cannot be accurately modeled.

C. Baseline Drift with Low Volatility Analytes

For low volatility analytes, such as nerve gas simulants, experiments were conducted to separate the electrical and chemical sources of baseline drift. The 20 ML CuPc device was employed for detecting nerve gas simulants using the 1% duty cycle, 0.1 Hz at −8V gate pulsing. The chemical responses to fifteen pulses of 19 ppm DIMP (simulant for Soman) and 32 ppm DMMP (simulant for Sarin) were taken. The chemical sensitivity to DIMP is $327.5+/-11.79 \times 10^{-3}$%/ppm with a drift of $1.15+/-0.73$%/h. The chemical sensitivity to DMMP is $178.7+/-4.9 \times 10^{-3}$%/ppm with a drift $0.45+/-0.1$%/h. The drifts for DIMP and DMMP are 12 and 5 times larger as compared to methanol using the same testing protocol.

To prove that the increased drift for DIMP and DMMP is due to to purely analyte induced drift, the chemical responses to DIMP pulses were recorded as a function of the recovery time. A longer recovery time allows a low vapor pressure analyte sufficient time to desorb from the device thereby reducing the analyte induced drift. The tests showed that the drift is reduced by 30 times to $0.036+/-0.007$%/h when the recovery time is increased to 3 h. Therefore, the increased drift in the presence of high boiling point analytes should be ascribed to analyte induced drift from accumulation of anlayte in the film during the time scale of the experiment. The tests showed that combining a low duty cycle analyte dose with a low duty cycle pulsed gating, the baseline drift for low vapor pressure analytes can be reduced to a level similar to those attained for highly volatile analytes.

The experiments showed that by pulsing the gate voltage at 0.1 Hz with a 1% duty cycle, the baseline drift has been reduced to 0.09%/h. The pulsed gating method also decreases the uncertainly in chemical sensing by an order of magnitude. The pulsed gating method has been found to be generally applicable to different channel materials, and for low vapor pressure nerve gas simulants when sufficient time is allowed for complete analyte desorption from the film via pulsed analyte gating.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A chemical sensor, comprising:
   a substrate;
   a gate electrode isolated from drain and source electrodes by gate dielectric;
   an organic ultra-thin semiconductor thin film arranged with respect to said gate, source and drain electrodes to act as a conduction channel in response to appropriate gate, source and drain potentials, said organic ultra-thin film being permeable to a chemical analyte of interest and consisting of one or a few atomic or molecular monolayers of material, wherein said thin film comprises one of the group consisting of copper phthalocyanine (CuPc), $CuC_{32}N_8H_{16}$, cobalt phthalocyanine (CoPc) and $CoC_{32}N_8H_{16}$, metal-free phthalocyanine ($H_2Pc$), $C_{32}N_8H_{18}$, and Copper-Hexadecafluorophthalocyanine ($F_{16}CuPc$ or $F_{16}CuC_{32}N_8H_{16}$).

2. The sensor of claim 1, wherein said thin film comprises one of copper phthalocyanine (CuPc) and $CuC_{32}N_8H_{16}$.

3. The sensor of claim 1, wherein said thin film comprises one of cobalt phthalocyanine (CoPc) and $CoC_{32}N_8H_{16}$.

4. The sensor of claim 1, wherein said thin film comprises one of metal-free phthalocyanine ($H_2Pc$) and $C_{32}N_8H_{18}$.

5. The sensor of claim 1, wherein said thin film comprises CuPc.

6. The sensor of claim 1, wherein said thin film comprises one of Copper-Hexadecafluorophthalocyanine ($F_{16}CuPc$ or $F_{16}CuC_{32}N_8H_{16}$).

7. The sensor of claim 1, wherein said thin film consists of less than 4 atomic or molecular monolayers of the material.

8. A sensor system comprising:
   a sensor chip having a plurality of sensors of claim 1;
   socket that mounts the sensor chip to a substrate and provides thermal and electrical interference isolation for the sensor chip; and
   sensing circuitry mounted on the substrate for controlling sensing operations conducted by the plurality of sensors.

9. A method of operating an organic thin film transistor chemical sensor, the method comprising:
   exposing the chemical sensor to a suspected analyte; and
   applying a low frequency and low duty cycle voltage pulse train to bias a gate electrode of the sensor to reduce baseline drift while sensing for a conduction channel change.

10. The method of claim 9, wherein said low duty cycle comprises about 10% or less.

11. The method of claim 10, wherein said low frequency comprises about 10 Hz or less.

12. The method of claim 9, wherein said low frequency comprises 0.1 Hz.

13. The method of claim 9, wherein said step of exposing comprises exposing the chemical sensor to low duty cycle pulses of the suspected analyte.

14. The method of claim 13, wherein said low duty cycle pulses of the suspected analyte comprise about 10% or less duty cycle pulses.

15. A method of fabricating an organic thin film transistor chemical sensor having a channel consisting of one or a few atomic or molecular monolayers, the method comprising:
   forming a dielectric on a substrate;
   forming a gate contact on the bottom of the substrate:
   forming tapered source and drain contacts while controlling the formation to avoid undercutting of the contacts;
   cleaning the source and drain contacts and gate dielectric via ultrasonication; and
   forming the one or a few monolayers of organic material over the gate dielectric and source and drain contacts.

16. The method of claim 15, wherein said step of cleaning comprises plural ultrasonications conducted in a sequence of trichloroethylene, acetone, and then isopropyl alcohol.

17. The sensor of claim 1, wherein said drain and source electrodes are tapered at a >90 degree angle relative to the gate dielectric and said thin film contacts the taper of said drain and source electrodes.

18. The method of claim 9, wherein the sensor comprises a substrate; a gate electrode isolated from drain and source electrodes by gate dielectric; an organic ultra-thin semiconductor thin film arranged with respect to said gate, source and drain electrodes to act as a conduction channel in response to appropriate gate, source and drain potentials, said organic ultra-thin film being permeable to a chemical analyte of interest and consisting of one or a few atomic or molecular monolayers of material.

\* \* \* \* \*

UNITED STATES PATENT AND TRADEMARK OFFICE
CERTIFICATE OF CORRECTION

PATENT NO. : 8,384,409 B2  
APPLICATION NO. : 12/597976  
DATED : February 26, 2013  
INVENTOR(S) : Kummel et al.

Page 1 of 1

It is certified that error appears in the above-identified patent and that said Letters Patent is hereby corrected as shown below:

Title Page, Other Publications:

Page 2, right column, line 8, delete "a." and insert --A.-- therefor.

In the Specification:

Col. 1, line 8  After "under" delete "pursuant to".

Col. 5, line 18  After "suitable" please delete "to".

Col. 8, line 58  After "chemical" please delete "sensor" and insert --sensors-- therefor.

Col. 9, line 32  Delete "$R = \dfrac{\Delta L}{I_{base}} = \dfrac{\Delta \mu}{\mu_{base}}$," and insert -- $R = \dfrac{\Delta I}{I_{base}} = \dfrac{\Delta \mu}{\mu_{base}}$ ,-- therefor.

Col. 9, line 61  Delete "takes" and insert --taken-- therefor.

Col. 11, line 61  After "CuPc" delete "device".

Signed and Sealed this  
Thirtieth Day of July, 2013

Teresa Stanek Rea  
*Acting Director of the United States Patent and Trademark Office*